(12) United States Patent
Win

(10) Patent No.: US 7,666,157 B2
(45) Date of Patent: Feb. 23, 2010

(54) SURGICAL PROTECTIVE TOOL POSITIONING APPARATUS

(76) Inventor: Jeff Win, No. 65, Tiansin Village, Yuanli Township, Miaoli County 358 (TW)

( * ) Notice: Subject to any disclaimer, the term of this patent is extended or adjusted under 35 U.S.C. 154(b) by 279 days.

(21) Appl. No.: 11/980,707

(22) Filed: Oct. 31, 2007

(65) Prior Publication Data
US 2009/0163843 A1    Jun. 25, 2009

(51) Int. Cl.
*A61F 5/00* (2006.01)
(52) U.S. Cl. .......................... 602/23; 602/27
(58) Field of Classification Search .............. 602/5, 602/23, 27–29; 128/882
See application file for complete search history.

(56) References Cited
U.S. PATENT DOCUMENTS

| | | | | |
|---|---|---|---|---|
| 4,771,768 A | * | 9/1988 | Crispin | .......... 602/16 |
| 4,974,583 A | * | 12/1990 | Freitas | .......... 602/24 |
| 5,078,128 A | * | 1/1992 | Grim et al. | .......... 602/23 |
| 5,329,705 A | * | 7/1994 | Grim et al. | .......... 36/88 |
| 5,368,551 A | * | 11/1994 | Zuckerman | .......... 602/23 |
| 5,464,385 A | * | 11/1995 | Grim | .......... 602/27 |
| 7,303,538 B2 | * | 12/2007 | Grim et al. | .......... 602/23 |

* cited by examiner

*Primary Examiner*—Michael A. Brown
(74) *Attorney, Agent, or Firm*—Rosenberg, Klein & Lee

(57) ABSTRACT

A surgical protective tool positioning apparatus includes a base, and two symmetric connecting bases disposed on the base, each having a containing groove formed by enclosing a first sidewall, a second sidewall, a third sidewall and a fourth sidewall. The second sidewall has a latch hole for interconnecting a containing space above the containing groove and the base for inserting a support stand downwardly into the containing groove. Each support stand has a latch lump latched to and protruded from the latch hole, such that each support stand is protected completely by the first sidewall, second sidewall, third sidewall and fourth sidewall of each connecting base to provide a better structural strength for connecting the support stand and the connecting base, and achieve the advantages of better durability and safety to the protective tool.

9 Claims, 8 Drawing Sheets

SURGICAL PROTECTIVE TOOL POSITIONING APPARATUS

BACKGROUND OF THE INVENTION

1. Field of the Invention

The present invention relates to a surgical protective tool positioning apparatus, and more particularly to a surgical protective tool positioning apparatus for protecting a human leg, ankle and foot.

2. Description of the Related Art

Referring to FIG. 7 for a section view of a portion of a prior art protective tool, the base 41 includes a support base 411 disposed on a side of the base 41, a concave portion 412 disposed on the support base 411, an opening 413 disposed on the concave portion 412 for inserting and connecting a support member 42 downwardly, and a plurality of positioning bolts 414 for positioning the support member 42 in the concave portion 412. In the method of using this protective tool, a user puts a patient's foot onto the base 41, and installs a wrapping member (not shown in the figure) into two support members 42 on both sides of the support base 411 and around the patient's lower leg.

In FIG. 7, when the support member 42 is inserted and connected into the concave portion 412, the support member 42 at the position of the opening in the lateral direction of the concave portion 412 still has insufficient protection, and the support member 42 is fixed by each positioning bolt 414 only. If a user moves sideway while a patient's limb is in contact with the ground at an instant moment or during walking, the support member 42 will fall off easily. Even after the wrapping member is wound, the support member 42 tends to separate easily from the opening in the lateral direction due to applying a force inappropriately. Therefore, a stable protection exists between the conventional support member 42 and support base 411 of the prior art only in a front-and-rear direction (which is called the Y direction) of the base 41, but the base 41 obviously has insufficient protection along its left-and-right direction (which is called the X direction).

Referring to FIG. 8 for a schematic view of a portion of another prior art protective tool, the protective tool includes a base (not shown in the figure), two corresponding connecting bases 5 (only one side is shown in the figure) and two support stands 6 (only one side is shown in the figure), wherein each connecting base includes a containing groove 51, whose top and lateral surfaces are open, two corresponding baffles 511 disposed on the lateral open surfaces of the containing groove 51, a latch stopping portion 512 disposed at the bottom of the containing groove 51. Each support stand 6 includes an inserting section 61, a latching portion 611 disposed separately on both sides of the inserting section 61, a hook 612 extended separately from two opposite directions and disposed on both lateral sides of the bottom of the inserting section 61, and a between the hooks 612 a turning member 613. The protective tool is installed as follows:

The inserting section 61 of the support stand 6 is inserted into the containing groove 51, and the two latching portions 611 of the inserting section 61 are stopped and limited at the position of the containing groove 51 by the two baffles 511, and the two latches 612 at the bottom of the inserting section 61 are latched to the latch stopping portion 512 at the bottom of the containing groove 51 and stopped at the bottom edge of the two baffles 511. When it is necessary to remove the protective tool, the turning member 613 is turned transversally outward from the lateral open surface of the containing groove 51, such that the two latches 612 are drawn close to each other in an internally drawn back condition, so as to release the two latches 612 from the bottom of the two baffles 511 and lift to remove the support stand 6.

Although this first kind of protective tools can overcome the shortcoming that the protective tool is insufficiently positioned by using the positioning bolt 414 to fix the support member 42, such prior art protective tool similarly has the insufficient protection, even if two baffles 511 have been installed at the external sides of the containing groove 51, and the connecting base 5 can provide protections to the support stand 6 along the X and Y directions (wherein X direction refers to the left-and-right direction of the base and Y direction refers to the front-and-rear direction of the base). Since each baffle 511 can be extended slightly from the walls of the containing groove 51, the structural strength of each baffle 511 is insufficient. In other words, the structural strength along the X direction of the connecting base 5 is insufficient. Similarly, each support stand 6 cannot be secured to each connecting base 5 when a patient's limb is in contact with the ground at an instant moment or during walking, and the support stand 6 will be separated laterally towards the outside of the containing groove 51, and thus the safety issue still exists.

Obviously, the connecting base of a traditional protective tool cannot provide a protection with complete and better structural strength with respect to the support stand, and thus the prior art is neither durable nor safe.

SUMMARY OF THE INVENTION

It is a primary objective of the present invention to overcome the foregoing shortcoming by providing a surgical protective tool positioning apparatus, wherein a connecting base of the protective tool is formed by enclosing a first sidewall, a second sidewall, a third sidewall and a fourth sidewall, and the connecting direction of the first and second sidewalls and the connecting direction of the third and fourth sidewalls constitute the protections along the X direction and the Y direction (transversal direction and longitudinal direction), so that the connecting base can have better structural strength to provide a higher stability for the connection when each support stand is inserted into each connecting base, so as to achieve the advantage of higher durability and safety.

To achieve the foregoing objective, the present invention comprises:

a base, having a vertical connecting base separately disposed on both left and right symmetric sides, and a containing space extended forward and backward between the connecting base and the base, and each connecting base having a first sidewall facing the exterior of the containing space and a second sidewall facing the interior of the containing space, and each connecting base having a third sidewall facing the front side of the base and a fourth sidewall facing the rear side of the base, and a containing groove being defined by enclosing the first sidewall, second sidewall, third sidewall and fourth sidewall, and each containing groove having an insert opening disposed at the top of each connecting base, and the second sidewall of each connecting base having a latch hole, and each containing groove being interconnected with the containing space through each latch hole;

two support stands, whose bottom having an inserting section of the containing groove of the connecting base inserted into the base, and a protruding section extended outwardly and parallelly with both lateral edges of the bottom of each inserting section, and the ends of the two protruding sections being connected by a connecting section for enclosing a pressing space, and an extended portion being extended from the connecting section towards the pressing space, and the extended portion having a latch lump protruded from a latch hole of the containing groove and corresponding to each connecting base of the base for latching into the latch hole, and the first sidewall and the second sidewall of each connecting base being connected to both left and right lateral surfaces of the inserting section of each support stand respectively, and the third sidewall and the fourth sidewall of each connecting base being connected to other two lateral surfaces of the inserting section of each support stand, which are both front and rear lateral surfaces of the inserting section for securing and positioning each support stand into the containing groove of each connecting base.

DETAILED DESCRIPTION OF THE PREFERRED EMBODIMENTS

Figure 1:
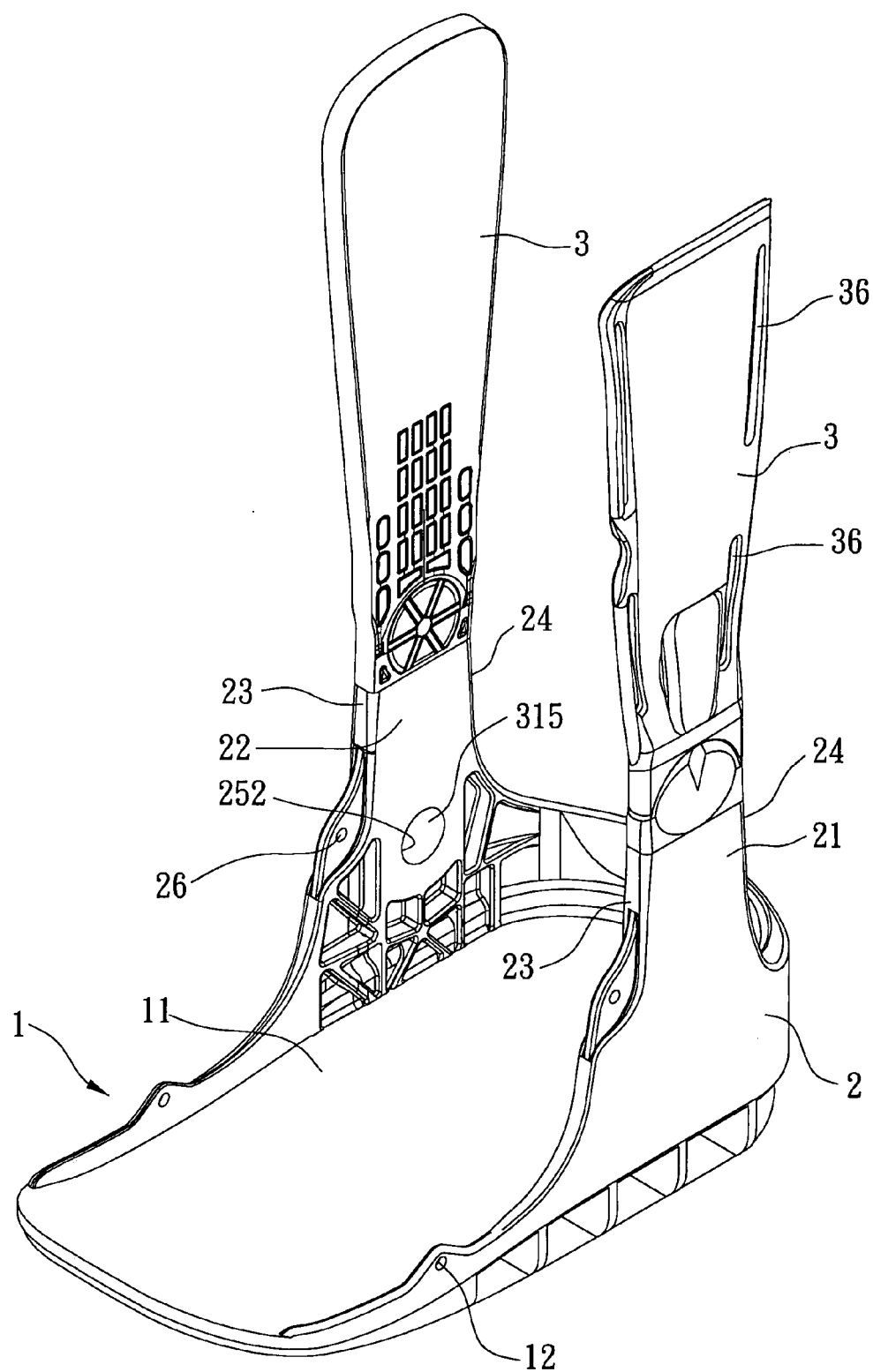
FIG. 1 is a perspective view of the present invention.

Referring to FIGS. 1 to 6 for the structures adopted by the preferred embodiments of the present invention, the embodiments are selected and used for illustrating the present invention only, but not intended to limit the scope of the invention.

Referring to FIGS. 1 to 4 for a surgical protective tool positioning apparatus in accordance with a first preferred embodiment of the present invention, the apparatus comprises:

a base 1, having a vertical connecting base 2 separately disposed on both left and right symmetric sides, and a containing space 11 extended forward and backward between the connecting base 2 and the base 1 and each connecting base 2 having a first sidewall 21 facing the exterior of the containing space 11 and a second sidewall 22 facing the interior of the containing space 11, and each connecting base 2 having a third sidewall 23 facing the front side of the base 1 and a fourth sidewall 24 facing the rear side of the base 1, and a containing groove 25 being defined by enclosing the first sidewall 21, second sidewall 22, third sidewall 23 and fourth sidewall 24, and each containing groove 25 having an insert opening 251 disposed at the top of each connecting base 2, and the second sidewall 22 of each connecting base 2 having a latch hole 252, and each containing groove 25 being interconnected with the containing space 11 through each latch hole 252;

two support stands 3, whose bottom having an inserting section 31 of the containing groove 25 of the connecting base 2 inserted into the base 1, and a protruding section 311 extended outwardly and parallelly with both lateral edges of the bottom of each inserting section 31, and the ends of the two protruding sections 311 being connected by a connecting section 312 for enclosing a pressing space 313, and an extended portion 314 being extended from the connecting section 312 towards the pressing space 313, and the extended portion 314 having a latch lump 315 protruded from a latch hole 252 of the containing groove 25 and corresponding to each connecting base 2 of the base 1 for latching into the latch hole 252, and the first sidewall 21 and the second sidewall 22 of each connecting base 2 being connected to both left and right lateral surfaces of the inserting section 31 of each support stand 3 respectively, and the third sidewall 23 and the fourth sidewall 24 of each connecting base 2 being connected to other two lateral surfaces of the inserting section 31 of each support stand 3, which are both front and rear lateral surfaces of the inserting section 31 for securing and positioning each support stand 3 into the containing groove 25 of each connecting base 2.

In this preferred embodiment, the latch lump 315 of each extended portion 314 forms an aslant guiding surface 315A at a position proximate to each connecting section 312, and each aslant guiding surface 315A is in contact with an internal edge of the second sidewall 22 at the position of the insert opening 251 of each connecting base 2 during an insertion, and the aslant guiding surface 315A of each latch lump 315 is provided for guiding and inserting the inserting section 31 of each support stand 3 into each containing groove 25.

Figure 2:
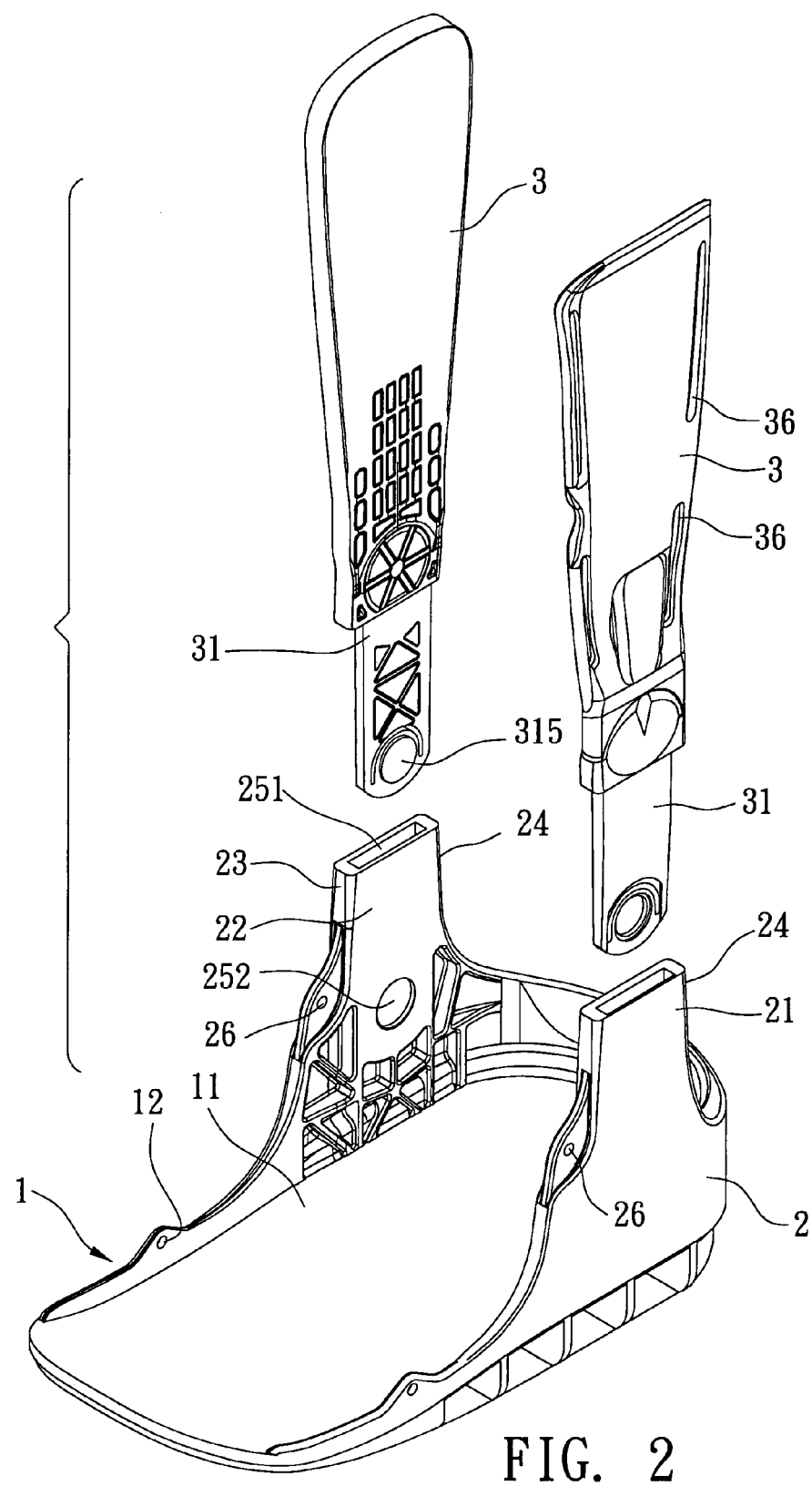
FIG. 2 is an exploded view of the present invention.
Figure 3:
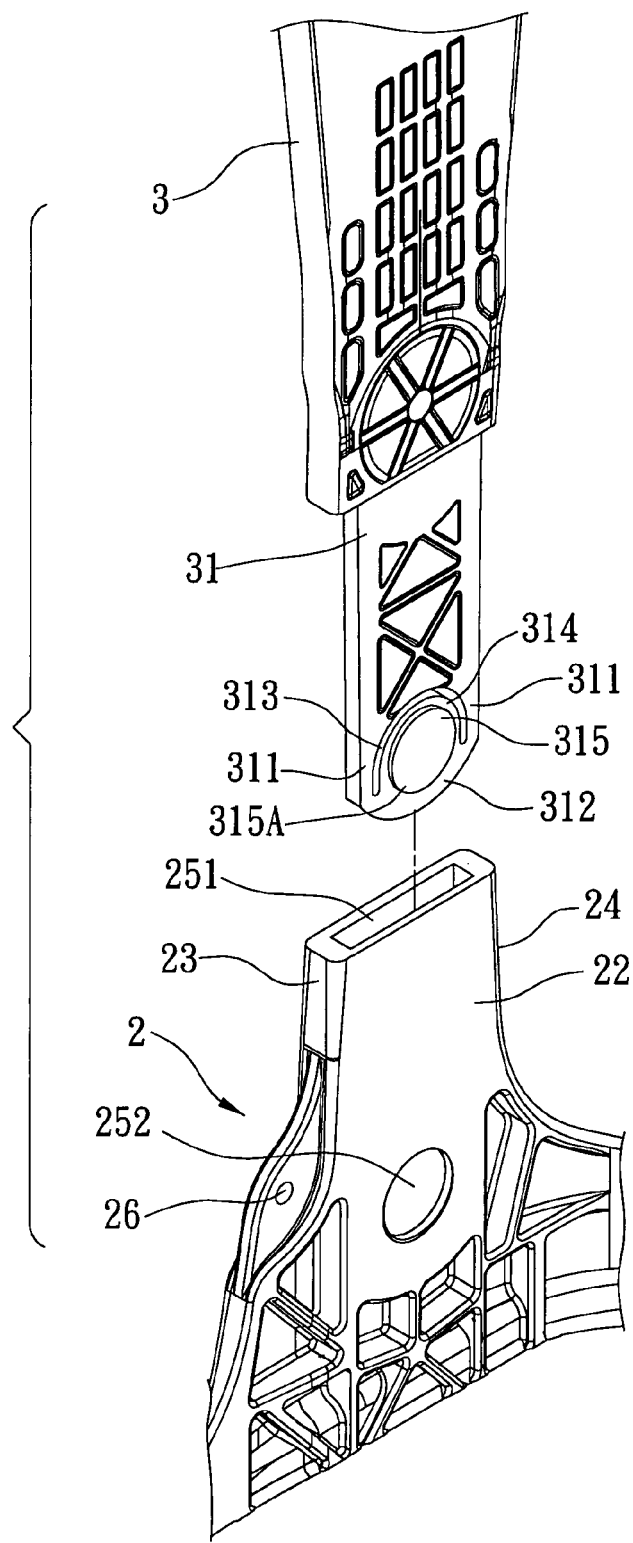
FIG. 3 is an enlarged view of a portion of a support stand being separated from a connecting base in accordance with the present invention.
Figure 4:
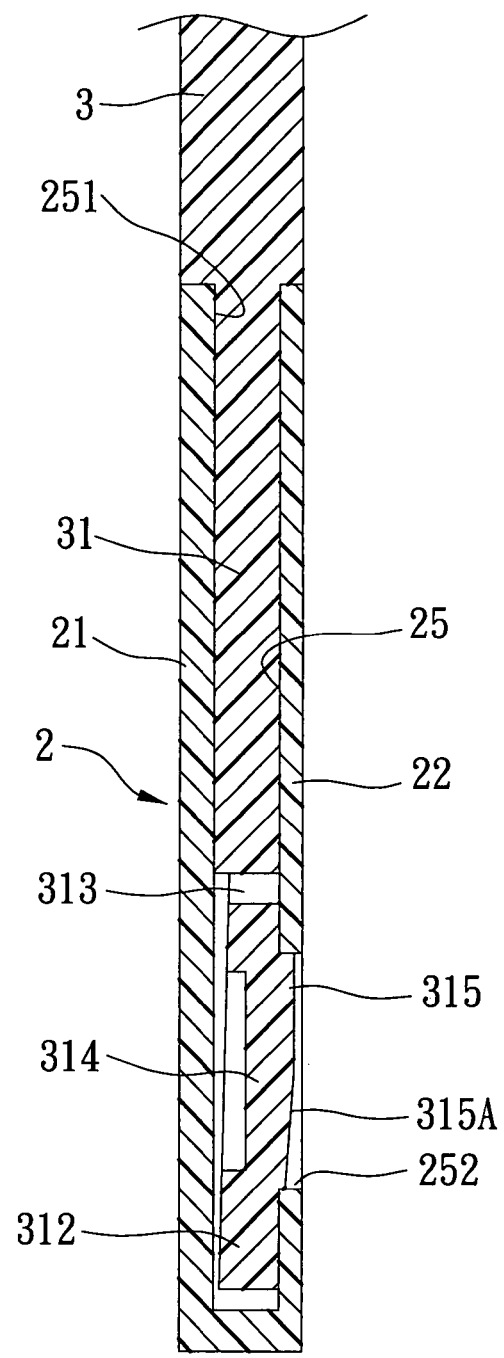
FIG. 4 is a section view of a support stand assembled in a connecting base in accordance with the present invention.

In FIGS. 2 and 3, the inserting section 31 of each support stand 3 is aligned precisely with the insert opening 251 of each connecting base 2 and inserted into each containing groove 25 for using the protective tool, and the latch lump 315 of the inserting section 31 of each support stand 3 is protruded and latched into the latch hole 252 of the second sidewall 22 of each connecting base 2, so that each support stand 3 can be secured into the containing groove 25 of each connecting base 2 as shown in FIGS. 1 and 4. On the other hand, if it is necessary to remove each support stand 3, the latch lump 315 on the extended portion 314 of the inserting section 31 of each support stand 3 is pressed, so that the latch lump 315 of each extended portion 314 is drawn backward with respect to the pressing space 313, and each latch lump 315 can be separated from each latch hole 252, and then each support stand 3 is pulled up to remove the inserting section 31 of each support stand 3 from each containing groove 25.

From the description above, the connecting direction of the first sidewall 21 and the second sidewall 22 of the connecting base 2 is defined as X direction (or transversal direction), and the connecting direction of the third sidewall 23 and the fourth sidewall 24 of the connecting base 2 is defined as Y direction (or longitudinal direction), such that when the inserting section 31 of each support stand 3 is inserted into each containing groove 25, each inserting section 31 is protected by each connecting base 2 along the X and Y directions. In other words, each connecting base 2 can be covered by its first sidewall 21, second sidewall 22, third sidewall 23 and fourth sidewall 24 to provide a protection with complete covering and sufficient structural strength for the inserting section 31 of each support stand 3 along the X direction (transversal direction) and the Y direction (longitudinal direction). In the present invention, after the inserting section 31 of each support stand 3 is connected to the containing groove 25 of each connecting base 2, the inserting section 31 will not be separated sideway easily as found frequently in the prior art.

Figure 5:
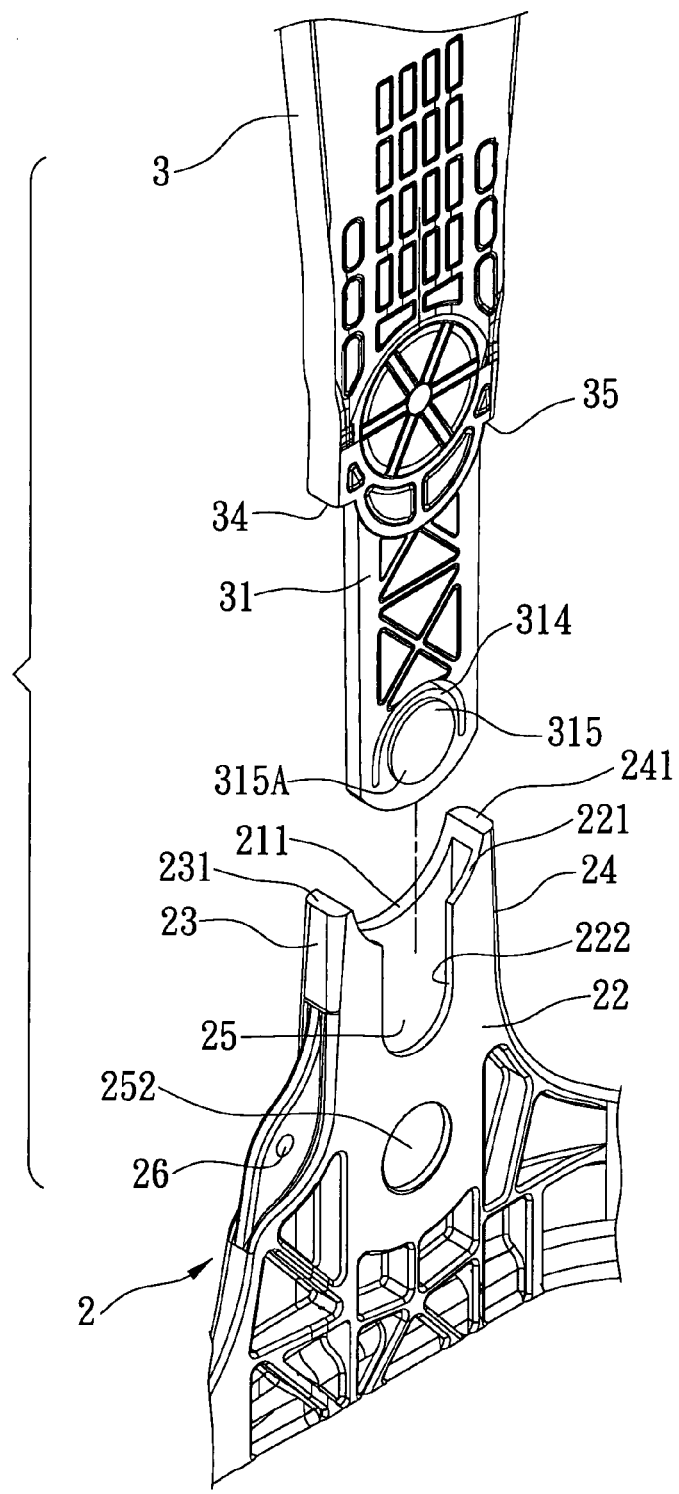
FIG. 5 is an enlarged view of a support stand being separated from a connecting base in accordance with a second preferred embodiment of the present invention.
Figure 6:
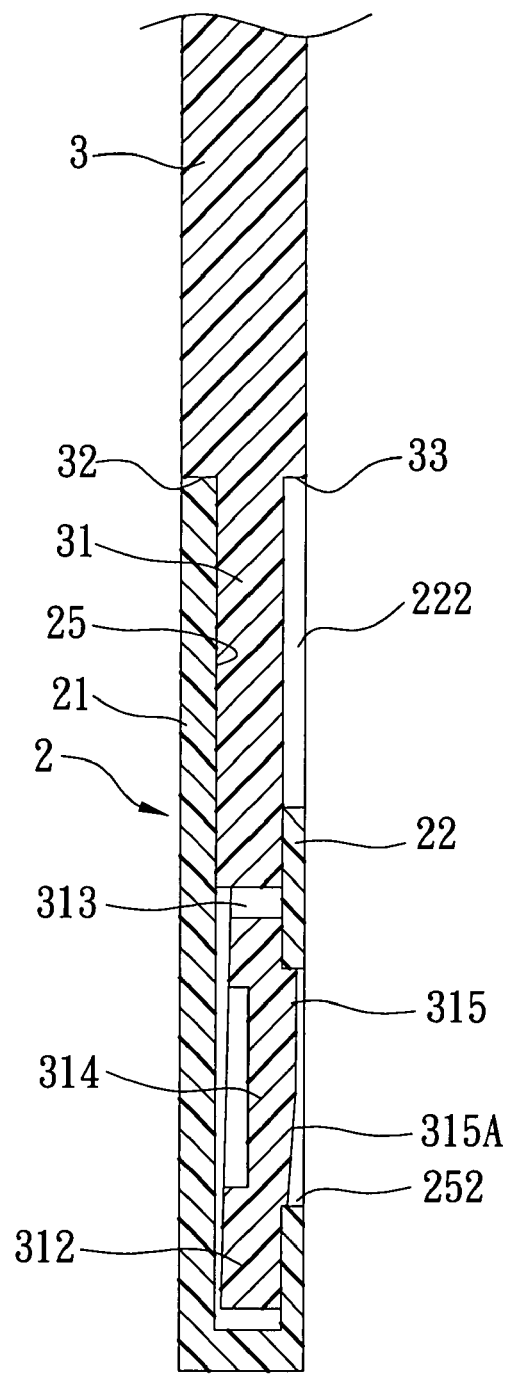
FIG. 6 is a section view of a support stand being assembled in a connecting base in accordance with a second preferred embodiment of the present invention.
Figure 7:
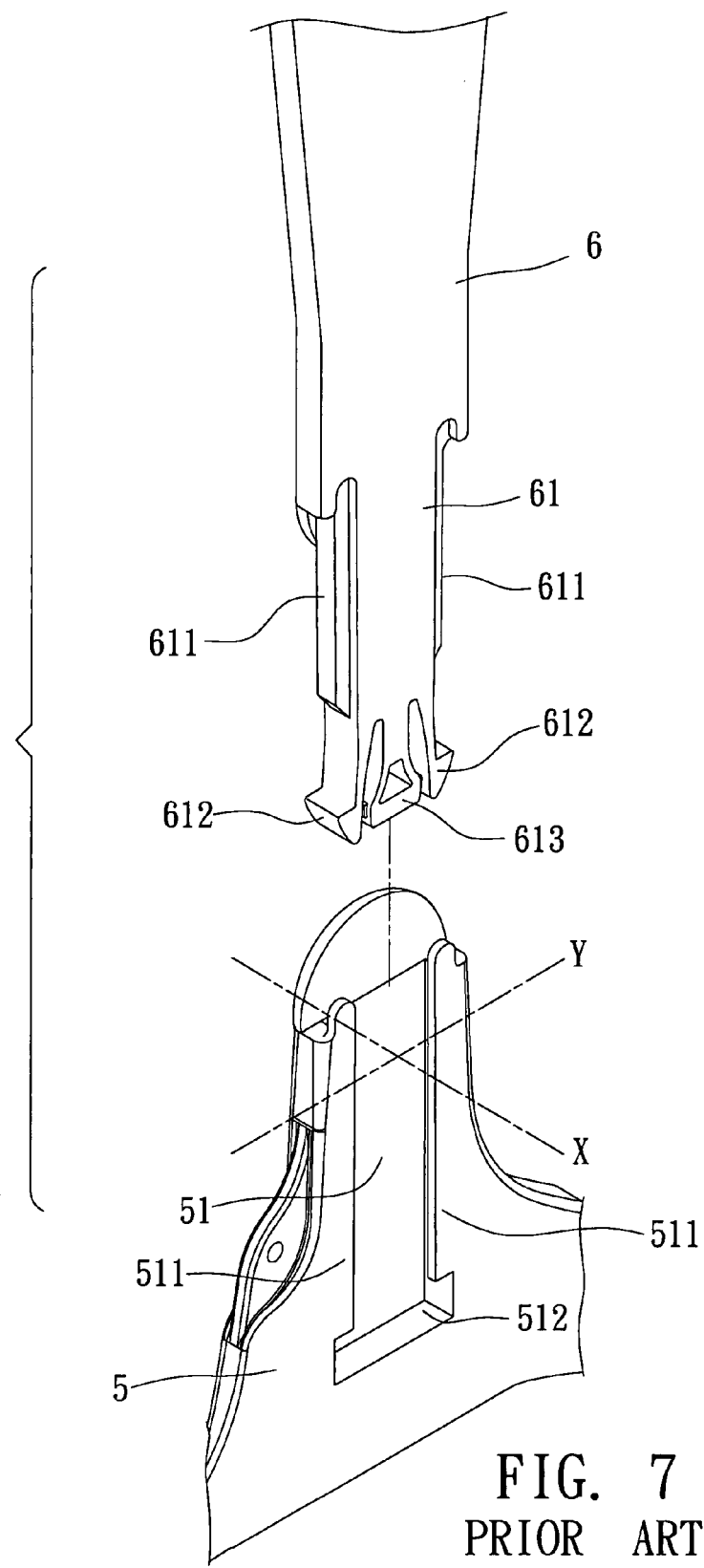
FIG. 7 is a schematic view of a portion of a prior art protective tool.
Figure 8:
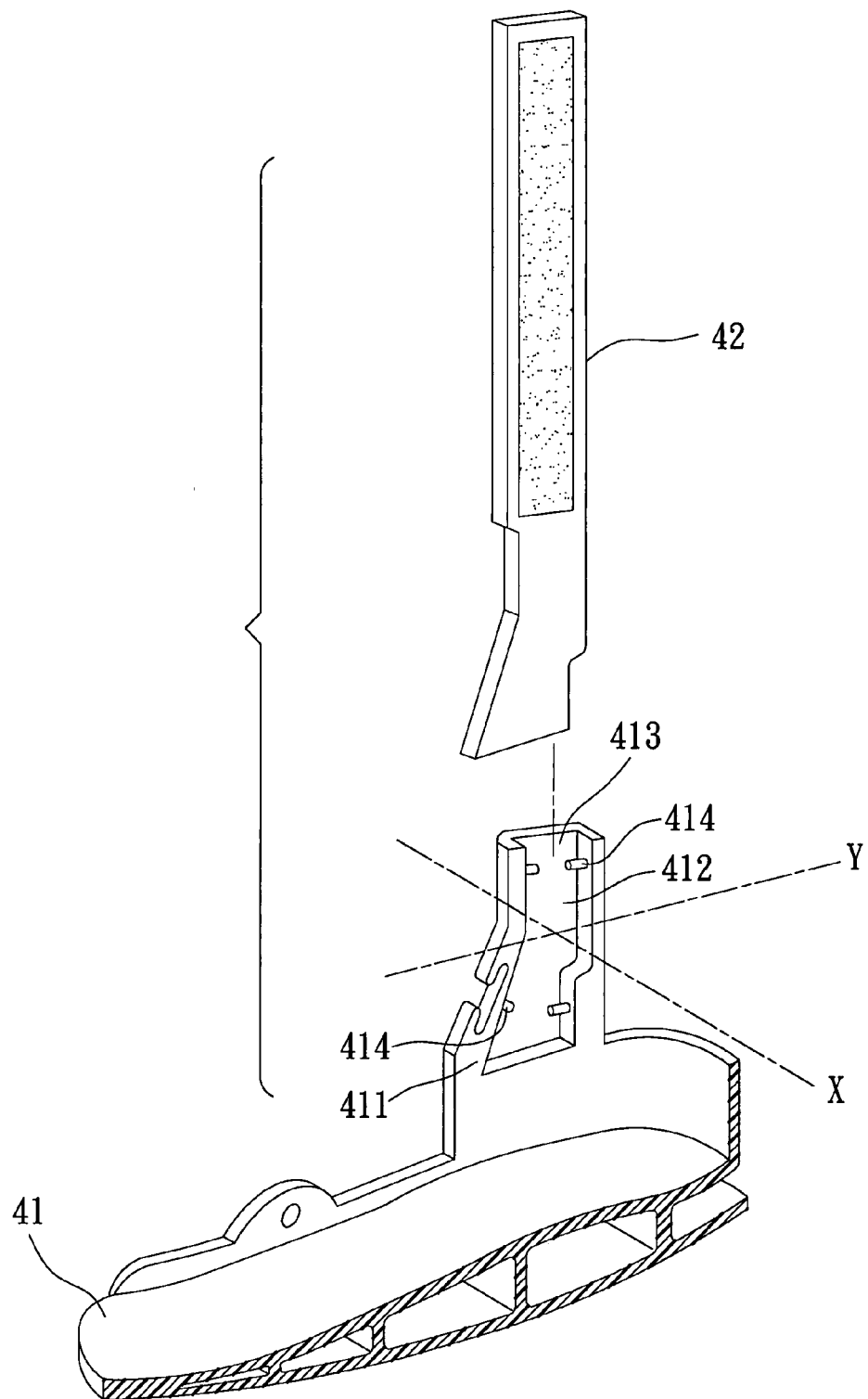
FIG. 8 is a schematic view of a portion of another prior art protective tool.

Of course, there are still many other examples of the present invention, but these examples are of minor modifications only. Referring to FIGS. 5 and 6 for a second preferred embodiment of the present invention, the first sidewall 21 and second sidewall 22 of each connecting base 2 have a positioning concave portion 211, 221 disposed concavely at the top of the first and second sidewalls 211, 221 respectively, and each support stand 3 includes a positioning protrusion 32, 33 disposed at a position corresponding to the positioning concave portion 211, 221 of the first sidewall 21 and the second sidewall 22, and each positioning protrusion 32, 33 and each positioning concave portion 211, 221 are pressed and connected with each other, and the positioning concave portion 221 of each second sidewall 22 has a a guide slot 222 disposed in the direction from the positioning concave portion 221 towards each latch hole 252, and the latch lump 315 of the extended portion 314 of each support stand 3 is protruded to and guided by the guide slot 222, and the latch lump 315 of each extended portion 314 forms an aslant guiding surface 315A at a position proximate to the connecting section 312, and each aslant guiding surface 315A is in contact with an internal edge of the second sidewall 22 at the bottom of each guide slot 222. In addition, the top of the third sidewall 23 and the fourth sidewall 24 of each connecting base 2 has a first stop portion 231, 241 respectively. Further, each support stand 3 includes a second stop portion 34, 35 disposed at two first stop portions 231, 241 corresponding to each connecting base 2, and the second stop portion 34, 35 of each support stand 3 and the first stop portion 231, 241 of each connecting base 2 are pressed and connected with each other.

In this preferred embodiment, the method is substantially the same as that of the first preferred embodiment, and the aslant guiding surface 315A of each latch lump 315 can guide the inserting section 31 of each support stand 3 into the each containing groove 25 through the guide slot 222 of each connecting base 2, and the positioning concave portion 211, 221 of each connecting base 2 and the positioning protrusion 32, 33 of each support stand 3 are connected, so that each support stand 3 and each connecting base 2 can be connected to provide better positioning effect.

In addition, the first stop portion 231, 241 of each connecting base 2 and the second stop portion 34, 35 of each support stand 3 are pressed and connected, so that each support stand 3 and each connecting base 2 have better positioning effect. Meanwhile, in the first preferred embodiment, each connecting base 2 provides better structural strength and protecting effect along the X direction (transversal direction) and the Y direction (longitudinal direction). In the second preferred embodiment, each connecting base 2 also provides better structural strength and protecting effect along the X direction (transversal direction) and the Y direction (longitudinal direction).

In the first and second embodiments of the preset invention, each connecting base 2 includes at least one through hole 26 disposed on a lateral edge towards the front of the base 1 for passing a wrapping member (not shown in the figure), and the base 1 also includes at least one through hole 1 disposed on a lateral edge proximate to each connecting base 2 for passing a wrapping member (not shown in the figure), and at least one of the two support stands 3 includes at least one through hole 36 for passing a wrapping member (not shown in the figure). The wrapping member is provided for connecting the through hole 36 of each support stand 3 and covering the two support stands 3 when a user puts a leg onto the base 1, so as to wrap and protect a patient's lower leg. In the meantime, the wrapping member can be connected to the through holes 12, 26 of the base 1 and the connecting base 2 to cover and protect the patient's instep.

In summation of the description above, the present invention provides better structural strength and protecting effect along the X direction (or transversal direction) and the Y direction (or longitudinal direction) between each connecting base and each support stand, and thus effectively overcome the durability and safety issues of the prior art.

What is claimed is:

1. A surgical protective tool positioning apparatus, comprising:

a base, having a vertical connecting base separately disposed on both left and right symmetric sides, and a containing space extended forward and backward between the connecting base and the base, and each connecting base having a first sidewall facing the exterior of the containing space and a second sidewall facing the interior of the containing space, and each connecting base having a third sidewall facing the front side of the base and a fourth sidewall facing the rear side of the base, and a containing groove being defined by enclosing the first sidewall, second sidewall, third sidewall and fourth sidewall, and each containing groove having an insert opening disposed at the top of each connecting base, and the second sidewall of each connecting base having a latch hole, and each containing groove being interconnected with the containing space through each latch hole;

two support stands, whose bottom having an inserting section of the containing groove of the connecting base inserted into the base, and a protruding section extended outwardly and parallelly with both lateral edges of the bottom of each inserting section, and the ends of the two protruding sections being connected by a connecting section for enclosing a pressing space, and an extended portion being extended from the connecting section towards the pressing space, and the extended portion having a latch lump protruded from a latch hole of the containing groove and corresponding to each connecting base of the base for latching into the latch hole, and the first sidewall and the second sidewall of each connecting base being connected to both left and right lateral surfaces of the inserting section of each support stand respectively, and the third sidewall and the fourth sidewall of each connecting base being connected to other two lateral surfaces of the inserting section of each support stand, which are both front and rear lateral surfaces of the inserting section for securing and positioning each support stand into the containing groove of each connecting base.

2. The surgical protective tool positioning apparatus of claim 1, wherein the latch lump of each extended portion forms an aslant guiding surface at a position proximate to the connecting section, and when each aslant guiding surface is inserted into and contacted with an internal edge of the second sidewall at the position of the insert opening of each connecting base, and the aslant guiding surface of each latch lump is provided for guiding and inserting the inserting section of each support stand into each containing groove.

3. The surgical protective tool positioning apparatus of claim 1, wherein each connecting base includes a positioning concave portion concavely disposed at the top of the first sidewall and the second sidewall, and each support stand includes a positioning protrusion separately disposed at a position of the positioning concave portion corresponding to the first sidewall and the second sidewall, such that each positioning protrusion and each positioning concave portion are pressed and connected with each other.

4. The surgical protective tool positioning apparatus of claim 3, wherein the positioning concave portion of each second sidewall includes a guide slot disposed at a center position and towards each latch hole, and the latch lump of the extended portion of each support stand is protruded to and guided by the guide slot.

5. The surgical protective tool positioning apparatus of claim 4, wherein the latch lump of each extended portion forms an aslant guiding surface at a position proximate to the connecting section, and each aslant guiding surface is in contact with an internal edge of the second sidewall at the bottom of each guide slot during an insertion.

6. The surgical protective tool positioning apparatus of claim 4, wherein each connecting base includes a first stop portion disposed at the top of the third sidewall and the fourth sidewall, and each support stand includes a second stop portion disposed separately on two first stop portions of each connecting base, and the second stop portion of each support stand and the first stop portion of each connecting base are pressed and coupled with each other.

7. The surgical protective tool positioning apparatus of claim 1, wherein each connecting base includes at least one through hole disposed at a lateral edge towards the front of the base for passing a wrapping member.

8. The surgical protective tool positioning apparatus of claim 1, wherein the base includes at least one through hole disposed at a lateral edge proximate to each connecting base for passing a wrapping member.

9. The surgical protective tool positioning apparatus of claim 1, wherein at least one of the two support stands includes at least one through hole for passing a wrapping member.

* * * * *